United States Patent [19]
Niznick

[11] Patent Number: 5,334,024
[45] Date of Patent: Aug. 2, 1994

[54] TRANSFER ABUTMENT

[75] Inventor: Gerald A. Niznick, Encino, Calif.

[73] Assignee: Core-Vent Corporation, Las Vegas, Nev.

[21] Appl. No.: 909,119

[22] Filed: Jul. 6, 1992

Related U.S. Application Data

[63] Continuation of Ser. No. 497,110, Mar. 21, 1990, abandoned.

[51] Int. Cl.⁵ .............................................. A61C 8/00
[52] U.S. Cl. ..................................... 433/173; 433/172
[58] Field of Search ............ 433/173, 174, 176, 201.1, 433/202.1, 172

[56] References Cited

U.S. PATENT DOCUMENTS

| | | | |
|---|---|---|---|
| 4,547,157 | 10/1985 | Driskell | 433/173 |
| 4,600,388 | 7/1986 | Linkow | 433/176 |
| 4,645,453 | 2/1987 | Niznick | 433/173 |
| 4,661,066 | 4/1987 | Linkow et al. | 433/176 |
| 4,713,003 | 12/1987 | Symington et al. | 433/173 |
| 4,854,872 | 8/1989 | Detsch | 433/173 |
| 4,955,811 | 9/1990 | Lazzara et al. | 433/173 |
| 4,960,381 | 10/1990 | Niznick | 433/173 |

FOREIGN PATENT DOCUMENTS

| | | | |
|---|---|---|---|
| 0288444 | 10/1988 | European Pat. Off. | 433/173 |
| 2635455 | 2/1990 | France | 433/174 |
| 2199502 | 7/1988 | United Kingdom | 433/174 |

Primary Examiner—John J. Wilson

[57] ABSTRACT

An abutment adapted for use with a dental implant includes a hollow tubular member of a size and shape adapted for use with an abutment or insert, and includes irregularities on its exterior surface that are adapted for engaging metals cast thereto. The tubular member has, at one end, a retention member for engaging a complementary retention member on the dental implant. The tubular member includes an internal passage adapted to receive a fastener for engaging a complementary fastener in the implant. The tubular member also includes an exterior sidewall portion adapted to form a positional transfer impression of the abutment in a dental cast.

11 Claims, 2 Drawing Sheets

TRANSFER ABUTMENT

This application is a continuation of application Ser. No. 07/497,110 filed Mar. 21, 1990, now abandoned, for "TRANSFER ABUTMENT" by GERALD A. NIZNICK.

BACKGROUND OF THE INVENTION

This invention relates to a combined transfer component and abutment adapted for use with a dental implant anchoring means.

SUMMARY OF THE INVENTION

This abutment includes a hollow tubular member of a size and shape adapted for use as an abutment or insert in a dental implant anchoring means such as the Core-Vent ® dental implant, the Screw-Vent ® dental implant, the Swede-Vent TM dental implant, and a Micro-Vent ® dental implant. This tubular member preferably has, on its exterior surface, irregularities adapted for engaging dental casting metals and alloys, such as gold alloys. The tubular member also has, at a first end, retention means for engaging complementary retention means on a dental implant. These retention means mate to, and lock with the complementary retention means in the implant. The tubular member includes an internal passage adapted to receive fastener means for engaging complementary fastener means in the implant. On its exterior sidewall portion, the tubular means includes means for forming a positional transfer impression of the abutment in a dental casting means. In preferred embodiments, this means comprises a flattened surface extending longitudinally along at least part of the exterior sidewall of the tubular member.

The retention means at the first end of the tubular member is adapted for engaging complementary retention means on the dental implant. For dental implants such as the Swede-Vent TM dental implant that have an exterior, multi-sided flange on their outer wall, the retention means comprises a multi-sided, complementary-shaped, inwardly tapering opening inside the passage in the tubular member. With dental implants that have an internal, irregularly-shaped, and preferably multi-sided passage for receiving abutments or inserts, the retention means comprises a complementary-shaped, preferably multi-sided, upwardly and outwardly tapering portion formed outside the passage at or near the first end.

The fastener means, in preferred embodiments, comprises shaft means having a threaded end portion adapted to engage a threaded passage inside a dental implant such as a Screw-Vent ® or Core-Vent ® dental implant. In preferred embodiments, the shaft means also includes a first, unthreaded portion having a first diameter, connected to a second, threaded portion of a second, smaller diameter. In preferred embodiments, adapted for use with this preferred embodiment of the fastener means, the passage means inside the tubular member includes, on its wall surface, flange means for engaging the end of the first portion of the shaft means and for preventing the shaft from passing through the passage.

The tubular member is preferably made from a heat-resistant metal or metal alloy that can withstand the heat from molten casting metal attached to the member. Preferably, the tubular member has a length in the range of about 8 to about 16 millimeters, and a diameter that approximates the diameter of the implant to be used with the member. Preferably, the tubular member has a wall sufficiently thin to allow room for the waxing and casting of metal to form a suitable prosthesis. Preferably, the tubular member has irregularities, such as score lines, on its outer surface, to provide mechanical retention for the casting metal that is applied to the tubular member for establishing contour.

The positional transfer means on the tubular member is adapted to transfer accurately the spatial and rotational position of the implant to which the abutment is to be joined. The transfer means maintains the same relationship to the retention means on the implant in the working dental cast as it had in the initial attachment of the abutment to the implant in the mouth, thus providing accurate transfer for the indirect technique of making a dental restoration.

The tubular member is preferably made of a high heat-resistant noble metal such as gold, palladium, platinum, titanium or an alloy of one or more of these metals. Titanium and titanium alloys are preferred because of their compatibility with the materials of the implant and their cost.

BRIEF DESCRIPTION OF THE DRAWINGS

The invention can better be understood by reference to the drawings, in which.

DETAILED DESCRIPTION OF THE PREFERRED DRAWINGS

Figure 1:
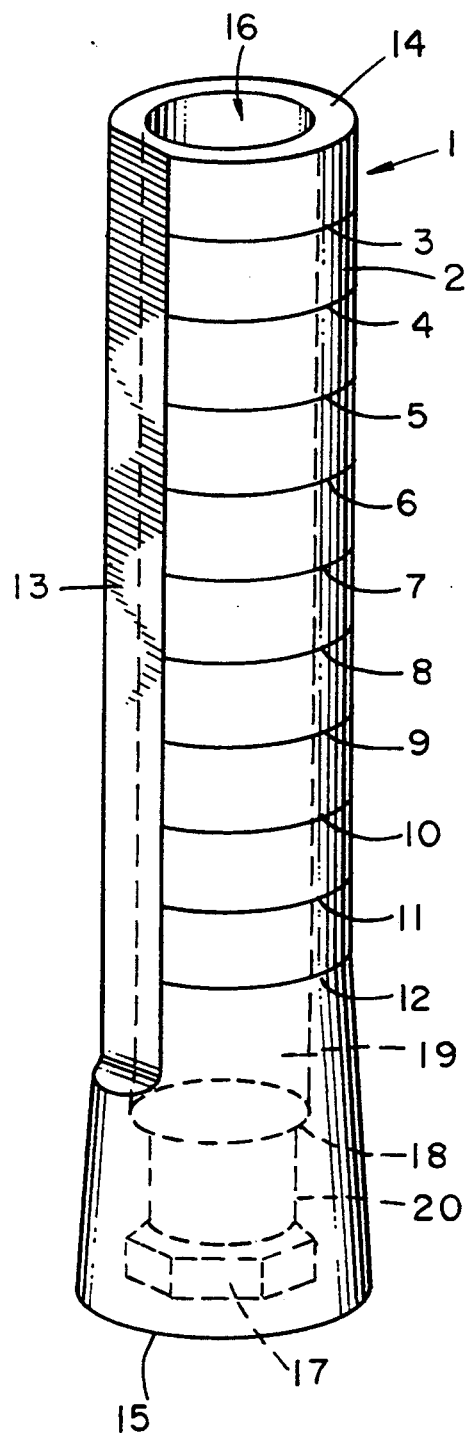
FIG. 1 shows a first embodiment of the tubular member of this invention adapted for use with a dental implant having external fastening means.

FIG. 1 shows tubular member 1 having external wall surface 2. Wall surface 2 includes a plurality of score lines 3, 4, 5, 6, 7, 8, 9, 10, 11 and 12 adapted for retaining metals cast thereto. Tubular member 1 also includes flattened sidewall portion 13, which extends longitudinally from upper end 14 along nearly the entire length of the tubular member towards second end 15.

Figure 3:
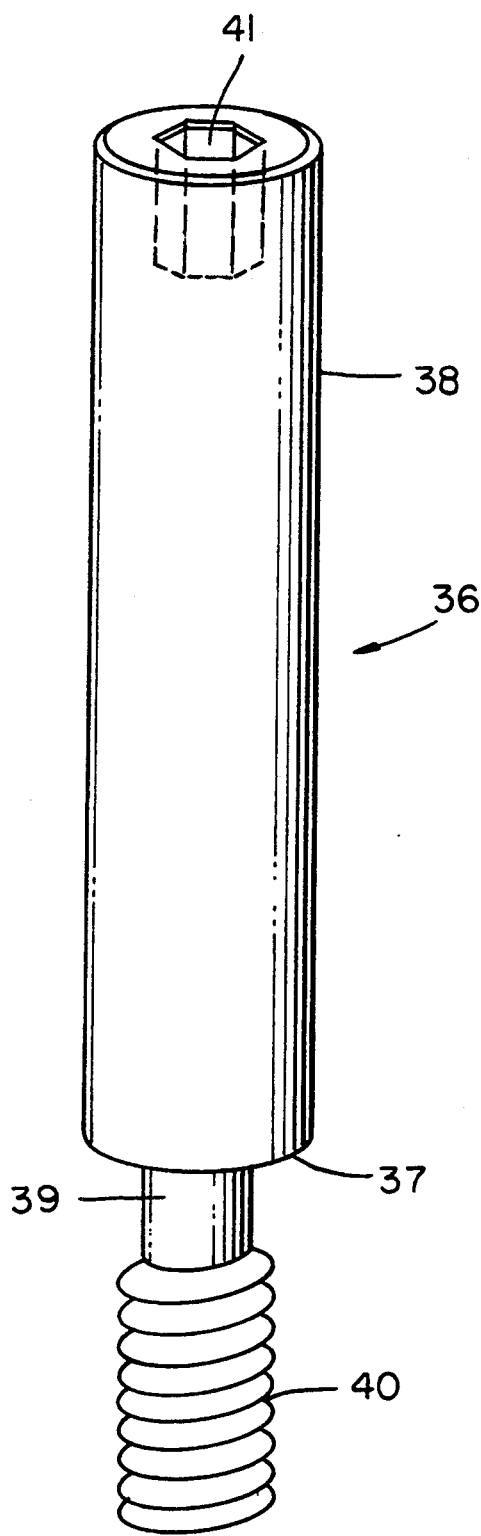
FIG. 3 shows a perspective view of the preferred embodiment of the threaded shaft member adapted for use with the tubular member embodiment shown in FIGS. 1 and 2.
Figure 4:
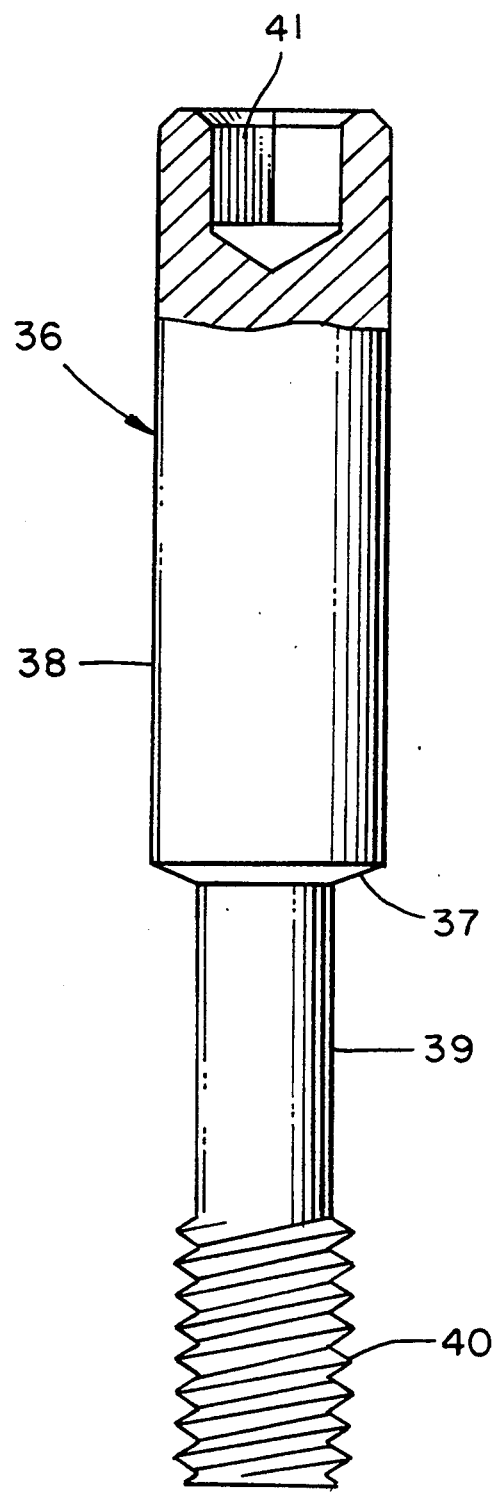
FIG. 4 shows a side elevation view of the shaft member shown in FIG. 3.

Tubular member 1 includes internal passage 16, which extends longitudinally entirely through tubular member 1. Opening 17 at end 15 of tubular member 1 is a multi-sided, inwardly tapering construction adapted to fit over, and lock onto an exterior fastening flange of complementary shape on the exterior of a dental implant such as a Swede-Vent TM dental implant. Internal passage 16 has two distinct portions, namely first portion 19, and second portion 20. Portion 19 is of greater diameter than portion 20, and ends in a flange 18, which engages a complementary threaded shaft that fits within passage 16, as seen in FIGS. 3 and 4. This shaft fits within passage 16, but is prevented from passing completely through the passage by engaging flange 18.

Figure 2:
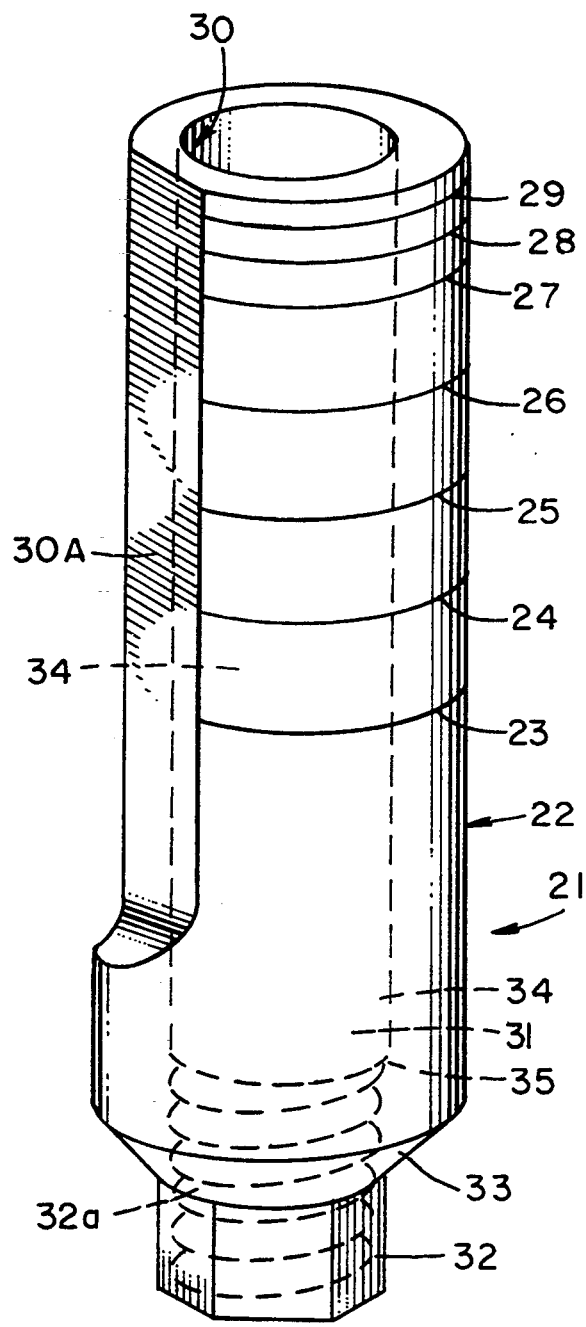
FIG. 2 shows a second embodiment of the tubular member of this invention, adapted for use with dental implants having internal fastening means.

FIG. 2 shows a second embodiment of a tubular member 21 of this invention. This tubular member also has on its exterior wall surface 22, a plurality of circumferential score lines 23, 24, 25, 26, 27, 28 and 29 for engaging metals cast thereto. Tubular member 21 also includes a flattened, longitudinally extending sidewall portion 30A to provide positional and spatial transfer when used in a casting process. The upper end of tubular member 21 includes an opening 30, which leads to passage 34 extending longitudinally through the interior of tubular member 21. At the other end of tubular member 21 is multi-sided portion 32, each side of which slants outwardly and upwardly toward connecting portion 33.

Portion 32 is adapted to be inserted into an internal, complementary-shaped, multi-sided opening at the top of an implant, and seats firmly therein as portion 32 is pushed into the implant opening. Internal passage 34 includes portions of two different diameters. First portion 31 has a first diameter, second portion 32a, a second, smaller diameter. These two sections 31 and 32a are connected to one another by a flange member 35 which engages the bottom end of shaft 36 at surface 37. Shaft member 36 has a first portion 38 whose diameter is slightly smaller than the internal diameter of first passage portion 19, and a second portion of smaller diameter 39 which passes through second passage portion 20 and section 33.

Threaded portion 40 at the bottom of shaft 39 is adapted to engage internal threads in a passage inside dental implants such as the Screw-Vent® dental implant or Core-Vent® dental implant. FIG. 4 shows more clearly surface 37, which seats on flange surface 35. At the top of shaft member 36 is multi-sided opening 41, which permits the threading of shaft member 36 into a dental implant by means of a suitable wrench or other tool.

What is claimed is:

1. An endosseous dental implant having an internal, multi-sided top opening wherein the sides of said internal top opening are substantially untapered, and are substantially parallel to the longitudinal axis of said endosseous dental implant, and an abutment adapted for use with said dental implant, said abutment including a hollow tubular member of a size and shape adapted for use as an abutment, said tubular member having, at one end, unthreaded retention means for anti-rotationally engaging, interlocking and interfitting with said internal, multi-sided top opening, said unthreaded retention means on said abutment tapering downwardly and inwardly from said one end and locking into said internal, multi-sided top opening when seated in said internal, multi-sided top opening, said tubular member including an internal passage adapted to receive fastener means for engaging complementary fastener means inside said implant.

2. The endosseous dental implant and abutment of claim 1 further comprising fastener means that comprises shaft means having a threaded end portion adapted to engage a threaded passage inside said implant.

3. The endosseous dental implant and abutment of claim 2 wherein said shaft means includes a first unthreaded portion having a first diameter connected to a second, threaded portion of a second, smaller diameter, and said passage includes, on its wall surface, flange means for engaging the end of said first portion and for preventing said shaft from passing through said passage.

4. The dental implant and abutment of claim 1 wherein said retention means comprises a multi-sided tapering end portion, said tapering end portion having at least two different perimeters spaced apart from one another on said tapering end portion.

5. An endosseous dental implant having an internal, multi-sided top opening wherein the sides of said internal top opening are substantially untapered and are substantially parallel to the longitudinal axis of said endosseous dental implant, and an abutment adapted for use with said endosseous dental implant, said abutment including a hollow tubular member of a size and shape adapted for use as an abutment, said tubular member having, at one end, unthreaded retention means for interfitting, anti-rotationally engaging and interlocking with said internal, multi-sided top opening in said implant, said tubular member including an internal passage adapted to receive fastener means for engaging complementary fastener means in said implant, said unthreaded retention means comprising a multi-sided portion outside said passage, said portion tapering outwardly toward said one end of said tubular member.

6. The dental implant and abutment of claim 5 further comprising fastener means that comprises shaft means having a threaded end portion adapted to engage a threaded passage inside said implant.

7. The dental implant and abutment of claim 6 wherein said shaft means includes a first unthreaded portion having a first diameter connected to a second, threaded portion of a second, smaller diameter, and said passage includes, on its wall surface, flange means for engaging the end of said first portion and preventing said shaft from passing through said passage.

8. The dental implant and abutment of claim 5 wherein said retention means comprises a multi-sided tapering end portion, said tapering end portion having at least two different perimeters spaced apart from one another on said tapering end portion.

9. An endosseous dental implant having an internal, multi-sided top opening wherein the sides of said internal top opening are substantially untapered and are substantially parallel to the longitudinal axis of said endosseous dental implant, and an abutment adapted for use with said endosseous dental implant, said implant having an at least partially threaded internal passage adapted to receive said abutment, said abutment having a size and shape adapted to support a dental prosthesis, said abutment having, at one end, unthreaded, tapered means for anti-rotationally engaging and interlocking with the sides of said internal, multi-sided top opening in said threaded internal passage, said abutment including an internal passage adapted to receive fastener means for engaging the threads in said threaded internal passage and for securing said abutment to the top of said implant.

10. The dental implant and abutment of claim 9 wherein said internal passage in said abutment is substantially tubular in shape, and extends substantially along the longitudinal axis of said abutment.

11. The dental implant and abutment of claim 9 wherein said retention means comprises a multi-sided tapering end portion, said tapering end portion having at least two different perimeters spaced apart from one another on said tapering end portion.

* * * * *